United States Patent [19]

Kwiatkowski et al.

[11] Patent Number: 5,688,971
[45] Date of Patent: Nov. 18, 1997

[54] PROCESS FOR PRODUCING DIKEGULAC, ITS SALTS AND DERIVATIVES

[75] Inventors: Stefan Kwiatkowski, Richmond; Miroslaw J. Golinski, Lexington, both of Ky.

[73] Assignee: PTRL East, Inc., Richmond, Ky.

[21] Appl. No.: 689,545

[22] Filed: Aug. 9, 1996

[51] Int. Cl.⁶ .................................................. C07D 493/00
[52] U.S. Cl. .............................................................. 549/361
[58] Field of Search ................................................. 549/361

[56] References Cited

U.S. PATENT DOCUMENTS

| | | | |
|---|---|---|---|
| 2,301,811 | 11/1942 | Reichstein | 260/344 |
| 3,043,749 | 7/1962 | Huang | 195/47 |
| 3,234,105 | 2/1966 | Motizuki et al. | 195/49 |
| 3,832,355 | 8/1974 | Jaffe et al. | 260/340.7 |
| 4,007,206 | 2/1977 | Szkrybalo | 260/340.7 |
| 4,337,080 | 6/1982 | Szkrybalo | 71/88 |

*Primary Examiner*—Johann Richter
*Assistant Examiner*—Ebenezer Sackey
*Attorney, Agent, or Firm*—King and Schickli

[57] ABSTRACT

A process is provided for producing dikegulac and its salts and derivatives from 2-keto-L-gulonic acid starting material.

3 Claims, No Drawings

PROCESS FOR PRODUCING DIKEGULAC, ITS SALTS AND DERIVATIVES

TECHNICAL FIELD

The present invention relates generally to a process for the preparation of di-O-isopropylidene-2-keto-L-gulonic acid (dikegulac) as well as its salts and related derivatives (e.g. esters).

BACKGROUND OF THE INVENTION

Dikegulac, its salts and related derivatives are well known in the art to be useful as plant growth regulators and/or herbicides. Methods for the preparation of dikegulac, its salts and related derivatives are described in, for example, U.S. Pat. Nos. 3,832,355 to Jaffe et al.; 4,007,206 to Szkrybalo and 4,337,080 to Szkrybalo.

The present invention relates to a novel method for the preparation of dikegulac, its salts and related derivatives, from 2-keto-L-gulonic acid. 2-keto-L-gulonic acid is an important, well known and readily available intermediate in the manufacture and production of vitamin C. It is derived from sorbitol which is first oxidized to L-sorbose by bacteria. The L-sorbose is then subjected to condensation with acetone in the presence of sulfuric acid followed by oxidation with permanganate and hydrolysis of the diisoprgpylidene derivative (dikegulac) by boiling in the presence of an acid. This procedure is described in, for example, U.S. Pat. No. 2,301,811 to Reichstein. Also, much more efficient and cost effective processes to directly produce 2-ketogulonic acid are known. They do not involve its diisopropylidene derivative (dikegulac) as an intermediate. Biochemical oxidation using Pseudomonas is described in U.S. Pat. No. 3,043,749 to Huang while biochemical oxidation using Pseudomonas and Acetobacter is described in U.S. Pat. No. 3,234,105 to Motizuki et al.

SUMMARY OF THE INVENTION

It is, accordingly, one object of the present invention to provide a new process for producing dikegulac, its salts and related derivatives utilizing readily available starting materials including 2-keto-L-gulonic acid, an important and readily available intermediate from the production or manufacture of vitamin C.

A further object of the present invention is to provide a safe and effective process for the efficient and economical production of dikegulac, its salts and related derivatives, well known to be useful as plant growth regulators and/or herbicides.

Other objects and advantages of the present invention will become apparent as the description thereof proceeds.

In satisfaction of the forgoing objects and advantages there is provided by this invention a process for producing dikegulac. The process comprises reacting 2-keto-L-gulonic acid

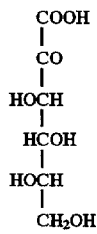

with a reagent selected from a group consisting of 2,2-dimethoxypropane and a mixture of 2,2-dimethoxypropane and acetone to produce a reaction intermediate having a chemical formula that is also known as an active agent.

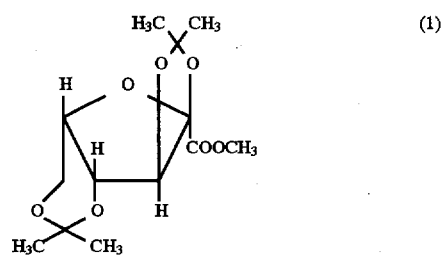

This is followed by the step of reacting the reaction intermediate of formula 1 with a base to complete saponification and produce an acid salt having a chemical formula

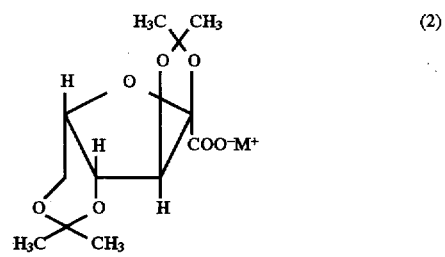

wherein $M^+$=sodium, potassium, ammonium, calcium, magnesium, copper as well as other members of the alkali and alkaline earth metal groups of the periodic table. The process may further include reacting the acid salt with an acid to produce dikegulac. Preferably, from a stand point of efficiency and cost of production the base utilized in the process is sodium hydroxide and the acid utilized is sulfuric acid.

DETAILED DESCRIPTION OF THE INVENTION

As indicated above, the present invention relates to a new and unique process for producing dikegulac, its salts and related derivatives. Dikegulac, many of its salts and many of its related derivatives provide post-emergent and/or pre-emergent plant growth regulant activity and herbicidal activity. Some specific applications of plant growth regulance of the type produced utilizing the present process include preventing lodging of cereals; increasing production of harvestable tea leaves by promoting side branching; inhibiting sprouting of potatoes and onions in storage; suppressing growth of grass, trees, shrubs and other vegetation in decorative lawn areas, parks, golf courses and along highways and other rights of way; accelerating fruit ripening and thus aiding mechanical harvesting by single or reduced number of pickings; defoliating cotton for mechanical harvest; inhibiting new growth of defoliated cotton and, thus, reducing standing of fiber during mechanical harvesting;

increasing the quality of the harvested crop, e.g. sugar content of sugar cane, sugar beets, grapefruit, grapes, and other fruits; aiding mechanical harvesting of nut crops by accelerating ripening, stimulating husk cracking and promoting abscission; protecting crops from drought; protecting fruit crops from frost by stimulating early dormancy and/or preventing premature breaking of dormancy; increasing latex flow of rubber; increasing frost resistance of winter cereals; reducing the flowering or bolting of lettuce, sugar beets and tobacco; controlling tobacco suckering; stimulating increased fruit set of soybeans, peanuts, cotton, tomatoes, melons and other fruits and enhancing fruit color and quality; stimulating branching of potted plants (e.g. heather, azalea, chrysanthemum, geranium); growth retardation in potted plants (e.g. poinsettia, petunia, chrysanthemum and azaleas); and stimulating branching of young fruit trees, (e.g. apple and pear).

Advantageously, dikegulac, its salts and related derivatives, are particularly useful for controlling the growth of grasses and weeds as well as undesired plants that become inadvertently mixed in with desired crops.

As is known in the art, uniform distribution of dikegulac, its salts and related derivatives, in order to control the growth of grasses and weeds may be achieved in a number of ways. The compound may be mixed with agriculturally acceptable adjuvants conventionally used for such applications in order to formulate solutions, emulsions, dispersions, dusts and/or wettable powders. Agriculturally acceptable adjuvants as utilized herein include inert carrier materials such as, for example, surface active agents, carriers, sticking agents, stabilizers, fillers, modifiers, diluents, conditioning agents and the like as well as other active agricultural materials including herbicides, fungicides, insecticides, and other plant growth regulants that compliment the activity of the compounds by enhancing the compounds activity or useful life.

Liquid formulations for the compounds adapted for direct spraying may, for example, be made as aqueous solutions or as solutions in solvent mixtures known for this purpose. Generally, such solutions are buffered (pH 5–7) by the addition of potassium hydrogen phosphate in order to better stabilize the compounds.

Emulsions may be prepared with 25–50% compound and surface active agents such as wetting agents, disbursing agents, emulsifying agents and the like in sufficient quantity to impart the desired characteristics to the formulation.

Wettable powder pre-mixes for the preparation of aqueous solutions may include from approximately 40–60% compound and 60–40% surfactant by weight.

Of course, the forms and rate of application of dikegulac, its salts and derivatives are very well known in the art.

In accordance with an important aspect of the present invention, dikegulac, its salts and related derivatives (e.g. esters) are prepared in a quick, efficient and effective process by reacting 2-keto-L-gulonic acid with a reagent selected from a group consisting of 2,2-dimethoxypropane and a mixture of 2,2-dimethoxypropane and acetone in order to produce a reaction intermediate having a chemical formula

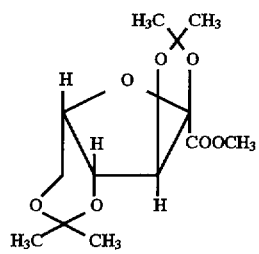

As noted above, 2-keto-L-gulonic acid is a well known and readily available intermediate in the manufacture of vitamin C. Accordingly, there is a ready source of this starting material.

Next is the step of reacting the reaction intermediate of formula 1 with a base (e.g. sodium hydroxide) to complete saponification and produce an acid salt having a chemical formula

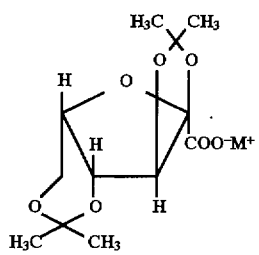

Of course, where sodium hydroxide is utilized as the base, $M^+$=sodium. It should be appreciated, however, that other bases may be utilized and $M^+$ may also be sodium, potassium, ammonium, calcium, magnesium, copper as well as other members of the alkali and alkaline earth metal groups of the periodic table. The dikegulac salts of formula 2 are known to be useful as plant growth regulators and herbicides. They, also, may be utilized as reaction intermediates in the production of related derivatives.

In accordance with the further aspect of the present invention, the acid salt of formula 2 may be reacted with an acid such as sulfuric acid in order to produce the compound dikegulac. Dikegulac is also useful as a plant growth regulator or herbicide. Dikegulac may also be utilized as an intermediate in the production of related useful derivatives.

The following synthesis and examples are presented to further illustrate the invention, but it is not to be considered as limited thereto.

EXAMPLE 1 i. Reaction of 2-keto-L-gulonic acid starting material to produce reaction intermediate of formula 1.

To a suspension of 97.1 g (0.5 mole) of 2-keto-L-gulonic acid starting material in a mixture of 400 ml of acetone and 400 ml of 2,2-dimethoxypropane (339 g, 3.253 mole, 6.51 equiv.) cooled to approximately 15° C. a solution of 18.4 g (10 ml) of sulfuric acid in 50 ml of acetone was added and the mixture was stirred at ambient temperature (21° C.) for 5 hours. The mixture was then added to a stirred suspension of 79.5 g (1.5 equiv.) of sodium carbonate in 100 ml of acetone and stirred for one hour (after approximately 15 minutes it became lighter in color). The mixture was then filtered to remove a fine white powder and concentrated under reduced pressure in a rotary evaporator to remove excess acetone and 2,2-dimethoxypropane and give 164.9 g of an oily product.

ii Purification of reaction intermediate having chemical formula 1.

To a solution of 142 g of the crude reaction intermediate of formula 1 (product of step i) in 216 ml of methanol at ambient temperature 15.1 ml of 2.0 N aqueous sodium hydroxide was added dropwise with stirring over a period of 25 minutes. After the addition was completed, the mixture was stirred for 50 minutes and an additional amount of 4.2 ml of 2.0 N aqueous sodium hydroxide was added over a period of 8 minutes. The mixture was then stirred for ½ hour and concentrated under a reduced pressure in a rotary evaporator (bath temperature 60° C.). The oily residue was then dissolved in 100 ml of acetone and 500 ml of ethyl ether was added in 25 ml portions while stirring. A solid precipitate was then filtered off and the filtrate was concentrated in a rotary evaporator and dissolved in 200 ml of ethyl ether (no precipitation). This solution was diluted with 200 ml of hexane that was added in 20 ml portions. The resulting mixture was filtered and the filtrate was concentrated to give 116.21 g of the desired ester as a light brown oil.

iii. Saponification of reaction intermediate of formula 1 to produce acid salt having chemical formula 2

The 116.21 g ester product of step ii was dissolved in 216 ml of methanol and saponified with 185 ml of 2N aqueous sodium hydroxide. During the addition of the sodium hydroxide, the mixture was stirred and cooled in an ice bath. The mixture was stirred at room temperature for an additional thirty minutes and then concentrated using a rotary evaporator (under reduced pressure at a bath temperature of 65° C.) to give 127 g (928.7 mmoles) of a glassy crude product. This product was triturated with 3L of boiling acetone for 30 minutes and then stirred at ambient temperature overnight. This reaction mixture was then filtered to collect 68.7 g of a solid acid salt of chemical formula 2.

iiii Converting acid salts of chemical formula 2 to dikegulac.

62.87 g of the acid salt of chemical formula 2 (product of the step iii) was dissolved in 106 ml of icy water and a solution of ice cold 1N sulfuric acid was added dropwise with stirring and external ice bath cooling at such a rate that the temperature did not rise above 3° C. After the addition was completed, an additional amount approximately 4 ml of ice cold 1N sulfuric acid was added to bring the pH to 2.28. A solid was then filtered off and washed with 2×50 ml of ice cold water. The solid was dried under 1 mm Hg vacuum to afford 57.4 g of pure dikegulac.

EXAMPLE 2

The process as set forth in Example 1 is performed with pure 2,2-dimethoxypropane substituted for the mixture of acetone and 2,2-dimethoxypropane in step i.

EXAMPLE 3

The process as set forth in Example 1 is performed with a methanolic solution of sodium hydroxide substituted for the aqueous sodium hydroxide in step ii. After any excess methanol is rotary-evaporated, the residue is dissolved in a small volume of acetone and inorganic by-products are precipitated with hexane. As a result, ethyl ether is no longer used in the process.

EXAMPLE 4

The process of Example 1 is performed with methanolic solution of sodium hydroxide substituted fox the aqueous sodium hydroxide of step iii. The salt is then precipitated by the addition of a small quantity of acetone.

In summary, a novel process has been disclosed for the preparation of dikegutac, its salts and related derivatives. Such compounds are useful as plant growth regulators and herbicides. The invention has been described herein with reference to certain preferred reagents and starting materials. It should be appreciated, however, that as obvious variations thereon become apparent to those skilled in the art, the invention is not to be considered as limited thereto.

We claim:

1. A process for producing dikegulac, comprising:
   reacting 2-keto-L-gulonic acid with 2,2-dimethoxypropane to produce a reaction intermediate having a chemical formula

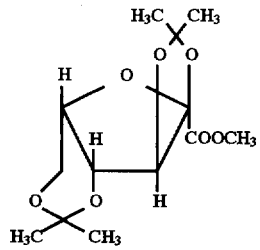

reacting said reaction intermediate with a base to complete saponification and produce an acid salt having a chemical formula

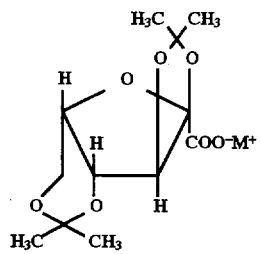

wherein $M^+$=sodium, potassium, ammonium, calcium, magnesium or copper.

2. The process set forth in claim 1 further including reacting said acid salt with an acid to produce dikegulac.

3. The process set forth in claim 2, wherein said base is sodium hydroxide and said acid is sulfuric acid.

* * * * *